US009244011B2

(12) United States Patent
Froggatt

(10) Patent No.: US 9,244,011 B2
(45) Date of Patent: Jan. 26, 2016

(54) METHOD AND APPARATUS FOR OFDR-BASED ELECTROPHORESIS

(71) Applicant: LUNA INNOVATIONS INCORPORATED, Roanoke, VA (US)

(72) Inventor: Mark E. Froggatt, Roanoke, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 60 days.

(21) Appl. No.: 14/358,951

(22) PCT Filed: Nov. 5, 2012

(86) PCT No.: PCT/US2012/063490
§ 371 (c)(1),
(2) Date: May 16, 2014

(87) PCT Pub. No.: WO2013/074314
PCT Pub. Date: May 23, 2013

(65) Prior Publication Data
US 2014/0300896 A1 Oct. 9, 2014

Related U.S. Application Data

(60) Provisional application No. 61/560,537, filed on Nov. 16, 2011.

(51) Int. Cl.
G01N 21/43 (2006.01)
G01N 21/53 (2006.01)
(Continued)

(52) U.S. Cl.
CPC .............. *G01N 21/53* (2013.01); *G01N 21/45* (2013.01); *G01N 27/44721* (2013.01); *B01D 57/02* (2013.01); *G01N 2030/746* (2013.01)

(58) Field of Classification Search
CPC .................... G01B 9/0209; G01B 9/02049
USPC ................................... 356/481, 517
See application file for complete search history.

(56) References Cited

U.S. PATENT DOCUMENTS 5,015,350 A 5/1991 Wiktorowicz
5,061,361 A 10/1991 Gordon
(Continued)

FOREIGN PATENT DOCUMENTS

EP 2 365 327 9/2011
KR 10-2007-0080048 8/2007
WO 2010/083269 7/2010

OTHER PUBLICATIONS

International Search Report for PCT/US2012/063490, mailed Mar. 18, 2013.
(Continued)

Primary Examiner — Jonathan Hansen
(74) Attorney, Agent, or Firm — Nixon & Vanderhye P.C.

(57) ABSTRACT

An optical interrogation system, e.g., an OFDR-based system, measures local changes of index of refraction of a medium contained within a light guiding tube and includes an optical interferometric interrogator, optical detection circuitry, and a data processor. The data processor initiates a sweep of the light source and guide light from an interrogating light source into a medium contained by a tube which restricts movement of particles provided into the tube, where the medium is subjected to a driving force that overcomes resistance to movement of particles through the medium in the tube. The optical interferometric interrogator provides an optical interference pattern associated with a group of particles having moved in the tube as a result of the driving force. Based on the optical interference pattern, the data processor identifies a current location of the group of particles in the tube.

32 Claims, 14 Drawing Sheets

(51) Int. Cl.
*G01N 21/45* (2006.01)
*G01N 27/447* (2006.01)
*B01D 57/02* (2006.01)
*G01N 30/74* (2006.01)

(56) References Cited

U.S. PATENT DOCUMENTS

| | | | |
|---|---|---|---|
| 7,515,276 B2 | 4/2009 | Froggatt et al. | |
| 2007/0014699 A1 | 1/2007 | Ratnayake et al. | |
| 2007/0229823 A1* | 10/2007 | Sung | G01N 15/1463 356/336 |
| 2009/0103100 A1 | 4/2009 | Froggatt et al. | |
| 2010/0225913 A1* | 9/2010 | Trainer | G01N 15/0205 356/338 |
| 2014/0146157 A1* | 5/2014 | Duplisea | H04N 7/18 348/79 |

OTHER PUBLICATIONS

Written Opinion of the International Searching Authority for PCT/US2012/063490, mailed Mar. 18, 2013.
International Preliminary Report on Patentability with Amended Sheets for PCT/US2012/063490, dated Feb. 24, 2014.
Extended European Search Report dated Jun. 2, 2015 in EP 12850246.5, 11 pages.

* cited by examiner

_US 9,244,011 B2_

METHOD AND APPARATUS FOR OFDR-BASED ELECTROPHORESIS

PRIORITY APPLICATION

This application is the U.S. national phase of International Application No. PCT/US2012/063490, filed on Nov. 5, 2012, which designed the U.S. and claims priority from U.S. provisional patent application Ser. No. 61/560,537, filed on Nov. 16, 2011, the contents of which are incorporated herein by reference.

TECHNICAL FIELD

The technology relates to electrophoresis-type measurements with many wide-ranging applications.

BACKGROUND

Electrophoresis is a process for separating a mixture of particles into separate groups of similar particles using the movement of ions in an electric field (drift currents). In capillary electrophoresis, a small tube (sometimes called a "capillary") with an inner diameter that is small enough to avoid turbulent flow is filled with an aqueous solution. A small amount of a mixture to be analyzed is provided at one end of the tube. An indicator stain or fluorescent marker may be included in the mixture to assist in resolving groups of particles after separation has occurred. A voltage, typically in the low tens of thousands of volts, is placed across the tube. Positive ions begin to move toward the negative electrode, and negative ions begin to move toward the positive electrode creating a current in the low tens of milliamps. The speed at which the ions move is determined by the size of the voltage (electric field), the charge on the ion, and the resistance to movement through the solution in the tube. Since different particles in the mixture have different resistances to movement, each type of particle moves at a different rate, and thus, the different particles begin to separate due to their differing resistances to movement. Over time, different and distinct particle groups form along the length of the tube. A group of the same particles, e.g., the same molecules, often appear in the shape of a plate or a band. Ultimately, electrophoresis is a stable way to separate a heterogeneous solution of particles into distinct individual particle groups.

FIG. 1 illustrates this electrophoresis process and shows a mixture of particles 12 introduced at one end of a capillary tube 10. As time progresses, the mixture separates into two distinct groups or groups of particles with one group 12A including one type of particle and the other group 12B including a second different type of particle. Each group is shown as a plate or band. Because one of these groups is faster than the other group, a separation distance develops. Once separated by a sufficient distance, the two groups may be identified and distinguished.

FIG. 2 illustrates an electrophoresis setup that includes probe light focused by a lens 14 through the tube 10 onto a stationary optical detector 16. The optical detector 16 detects each group as it crosses a detector zone that includes probe light and a focusing lens. Typically, only one location along the tube 10 is monitored. An output of a capillary electrophoresis instrument coupled to the detector 16 may be a plot of detected material, e.g., by UV fluorescence or absorbance, as a function of time. FIG. 3 is an illustration of an example capillary electrophoresis plot with peaks arriving over the course of 1 to 10 minutes.

In the case of fast moving molecules, gel electrophoresis is implemented to increase the resistance to movement for the molecules. Similar to the first example, groups of particles migrate down a tube under a voltage and the gel ensures separation can be achieved before the particles reach the end of the tube by supplying a higher resistance to movement. A drawback of gel type and other known electrophoresis techniques is that they are time consuming. A significant amount of time must be waited before each group of particles passes the detection location, and this time period is even longer when a higher resistive transportation medium is used in the tube. For example, FIG. 4 shows a spatial distribution of three different groups of particles at 3 minutes into the test. It would be desirable to identify the individual groups as they separate and move down the capillary tube before reaching the single detection location in order to speed up the process.

In addition to long processing times, known technology suffers from a limited detection region. As seen in FIG. 2, a typical setup consists of a single monitoring location. This is due to the complexity of setting up additional detection points as each requires a probe light, focusing lens, and detection system. This location must be monitored continuously, and without interruption, as particles that pass that detection location when the system is not monitoring the location will have no means of being detected as they progress in a single direction through the tube. This causes multiplexing of several sample tubes to be impractical, as a sample may be missed as another tube is being monitored. Another problem is that single point scanning approach requires that the length of the capillary tube be determined before the contents and separation rate of the various particles are known.

The inner diameter of the capillary tube is also restricted in current techniques. As the inner diameter decreases, optical detection becomes more difficult because the path through the solution becomes smaller as well. Reduced path length means a lower number of particles will exist in the volume requiring higher concentrations for successful detection. It is desired in the technique to use smaller tubes. As the inner diameter decreases, there is less current carried by the solution, and thus, less heat dissipation. Further, whatever heat is generated is more quickly moved out of the solution and into the tube wall. Lower temperature means less thermal diffusion and better resolution of the particle groups. The ability to use smaller capillary inner diameters means that high separation rates (due to higher voltages) can be achieved with better resolutions (due to lower temperatures).

SUMMARY

An optical interrogation system measures local changes of index of refraction of a medium contained within a light guiding tube. The system includes an optical interferometric interrogator, optical detection circuitry, and a data processor. The data processor initiates a sweep of the light source and guide light from an interrogating light source into a medium contained by a tube which restricts movement of particles provided into the tube, where the medium is subjected to a driving force that overcomes resistance to movement of particles through the medium in the tube. The optical interferometric interrogator provides an optical interference pattern associated with a group of particles having moved in the tube as a result of the driving force. One example of the optical interference pattern is a scattering profile. Based on the optical interference pattern, the data processor identifies a current location of the group of particles in the tube.

In preferred example embodiments, the optical interrogation system is an optical frequency domain reflectometry (OFDR)-based system, the interrogating light source is a tunable laser, and the detected optical interference pattern indicates back scatter amplitude as a function of time along the tube. The driving force causes a first group of particles in the medium to move through the tube at a different speed than a second different group of particles in the medium, and wherein the data processor is configured to detect a first location of the first group of particles in the tube medium and a second location of the second group of particles in the tube medium based on different optical interference patterns detected for the first and second groups. Each of the first and second groups of particles causes a local change in index of refraction of the medium and the local change in index of refraction changes the optical interference pattern as compared to a reference optical interference pattern. The data processor identifies the location of each of the first and second group of particles in the tube based on the changed optical interference pattern.

In one example implementation, the OFDR system detects multiple optical interference patterns corresponding to multiple different locations along the tube, where each detected optical interference pattern indicates a change in optical phase as a function of time along the tube.

In one example implementation, the tube is made of a first material having a first index of refraction and an inner ring of a second material having a second, higher index of refraction. In another example implementation, the tube includes an array of holes parallel to and adjacent an inner ring of the tube. In yet another example, the inside of the tube includes one or more Bragg gratings. In yet another example, the inside surface of the tube includes defects and wherein the data processor is configured to process back scatter from the defects to identify local changes in index of refraction.

Other example embodiments include multiple tubes being optically coupled to the optical interrogation system. The OFDR data processor initiates a sweep of the light source and guide light from the interrogating light source into the medium contained by each tube and detects via the optical interferometric interrogator an optical interference pattern associated with a group of particles having moved in each tube. Then, based on the detected optical interference patterns, it identifies a current location of the group of particles in each of the multiple tubes. The multiple tubes can be for example an array of tubes.

A method for measuring local changes of index of refraction of a medium contained within a light guiding tube using an optical interrogation system is also described. Particles are provided into a tube containing a medium that restricts movement of the particles. The medium in the tube is subjected to a driving force that overcomes resistance to movement of particles through the medium in the tube. Light from an interrogating light source is guided into the tube, and an optical interferometric interrogator detects an optical interference pattern associated with a group of particles having moved in the tube as a result of the driving force. Based on the detected optical interference pattern, a current location of the group of particles in the tube is identified. Multiple optical interference patterns corresponding to multiple different locations along the tube may be detected. The method may be used for multiple tubes coupled to the optical interrogation system to identify a current location of the group of particles in each of the multiple tubes.

In example embodiments, an environment surrounding the tube is modified to change a response of one or more particle groups in the tube. Thereafter, a characteristic of the one or more particles in one of the particle groups is identified based on an optical interference pattern detected from the tube subjected to the modified environment. For example, modifying the environment includes one or more of modifying temperature, pH, and/or magnetic field.

In other example embodiments, one or more properties of the transportation medium with the tube are modified. A characteristic of the one or more particles in one of the particle groups is identified based on an optical interference pattern detected from the tube after the transportation medium is modified.

DETAILED DESCRIPTION

Figure 1:
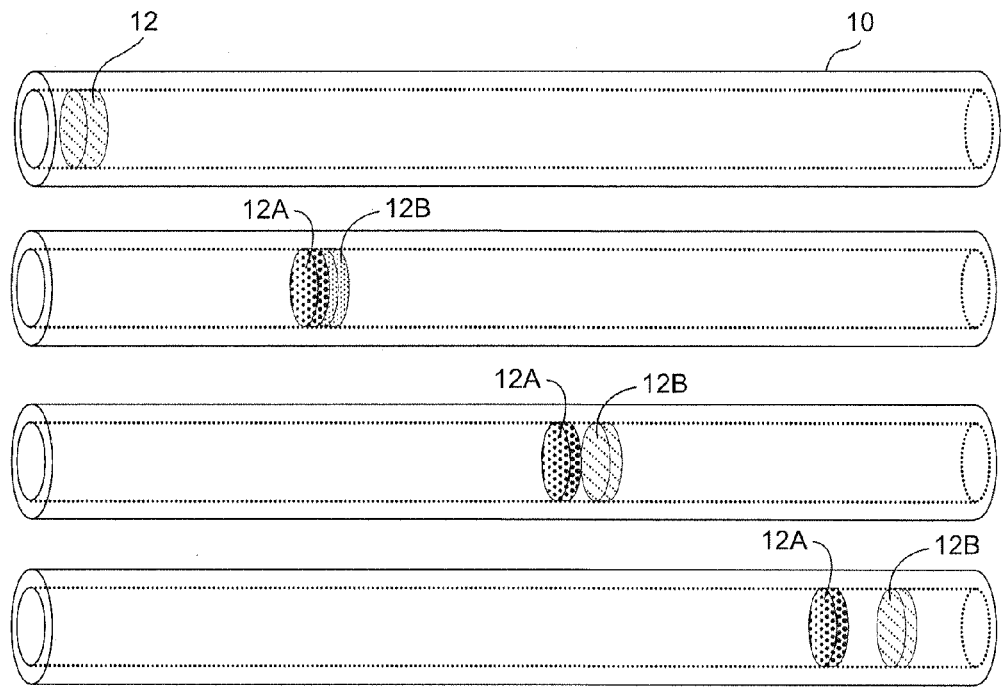
FIG. 1 illustrates separation of "plates" or groups of material, e.g., particles, in a mixture (referred to general as groups of particles) in a capillary tube in electrophoresis.
Figure 2:
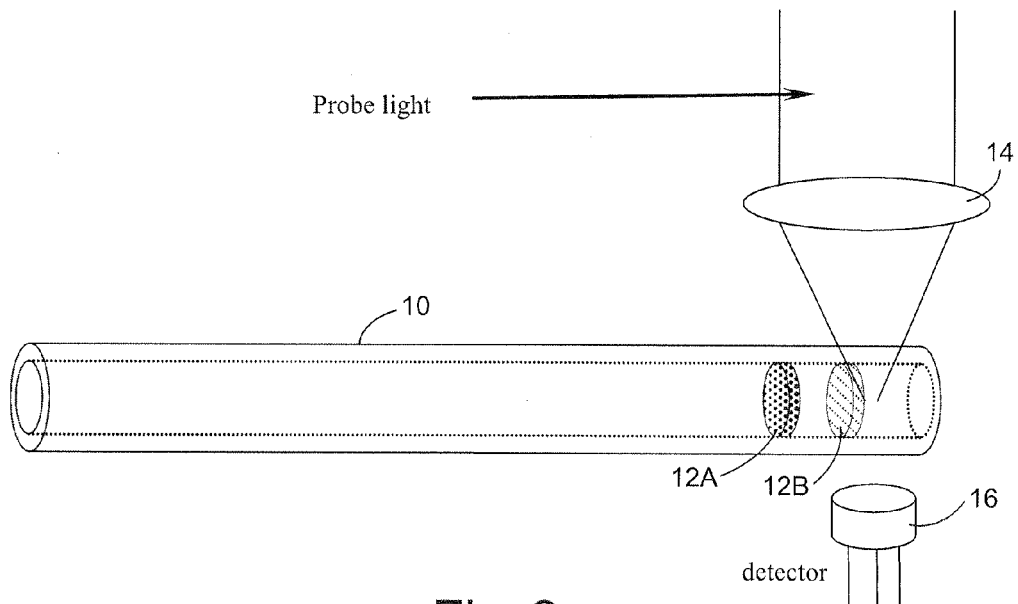
FIG. 2 illustrates an optical stationary detector that detects the plates as they cross the detector zone.
Figure 3:
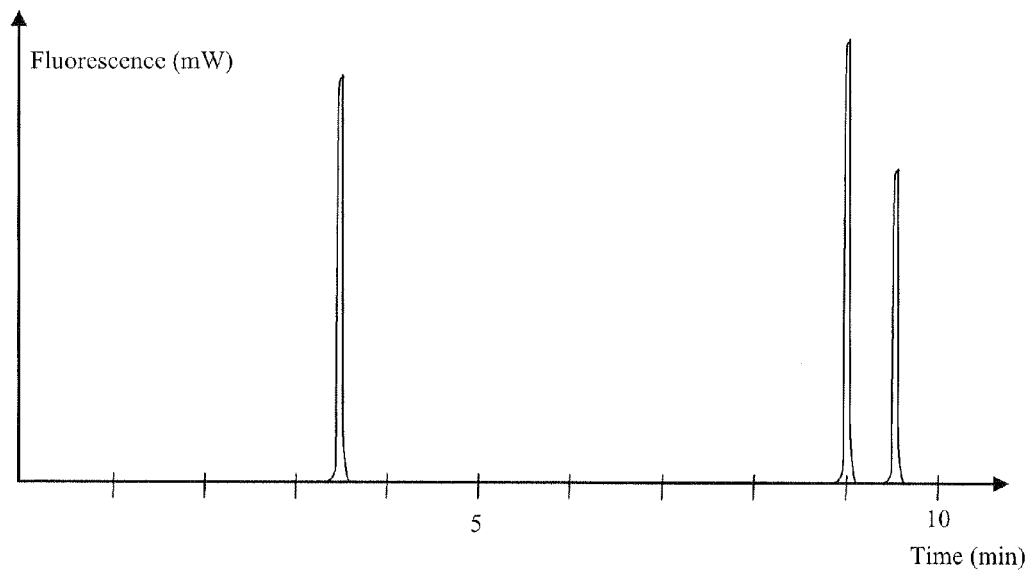
FIG. 3 is a graph illustrating the output from a capillary electrophoresis measurement.
Figure 4:
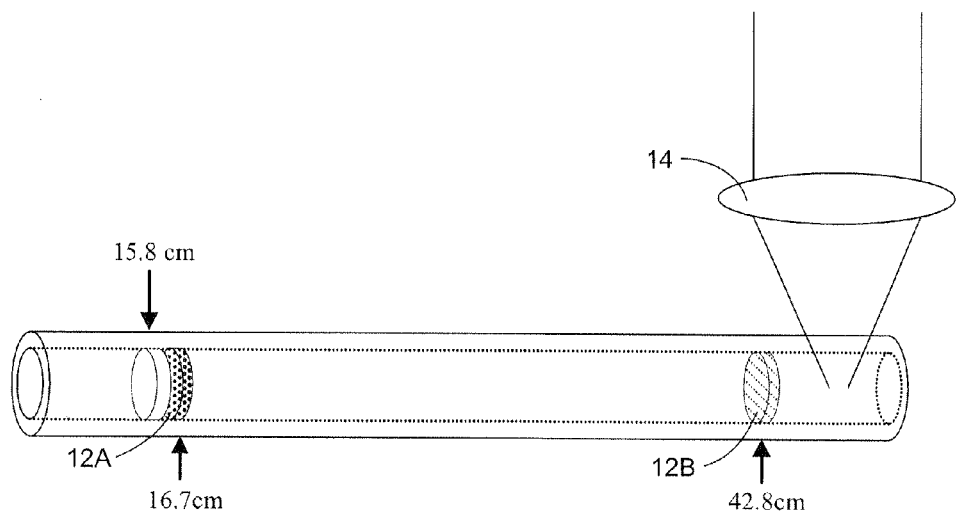
FIG. 4 illustrates the spatial distribution of the material at 3 minutes into the test shown in FIG. 3.

The following description sets forth specific details, such as particular embodiments for purposes of explanation and not limitation. But it will be appreciated by one skilled in the art that other embodiments may be employed apart from these specific details. In some instances, detailed descriptions of well known methods, interfaces, circuits, and devices are omitted so as not obscure the description with unnecessary detail. Individual blocks are shown in some figures. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and data may be stored on a non-transitory, computer-readable storage medium, and when the instructions are executed by a computer or other suitable processor control, the computer or processor performs the functions associated with those instructions.

Thus, for example, it will be appreciated by those skilled in the art that diagrams herein can represent conceptual views of illustrative circuitry or other functional units. Similarly, it will be appreciated that any flow charts, state transition diagrams, pseudocode, and the like represent various processes which may be substantially represented in computer-readable medium and so executed by a computer or processor, whether or not such computer or processor is explicitly shown.

The functions of the various illustrated blocks may be provided through the use of hardware such as circuit hardware and/or hardware capable of executing software in the form of coded instructions stored on computer-readable medium. Thus, such functions and illustrated functional blocks are to be understood as being either hardware-implemented and/or computer-implemented, and thus machine-implemented.

In terms of hardware implementation, the functional blocks may include or encompass, without limitation, a digital signal processor (DSP) hardware, a reduced instruction set processor, hardware (e.g., digital or analog) circuitry including but not limited to application specific integrated circuit(s) (ASIC) and/or field programmable gate array(s) (FPGA(s)), and (where appropriate) state machines capable of performing such functions.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

The technology in this application provides an OFDR-based method and apparatus for determining the location of different particles or groups of particles along the length of a tube subjected to an electric field over time that requires no staining and can be constantly updated as the material disperses under the electric field. A particle is a small localized object to which can be ascribed physical properties such a volume or mass. A group of particles includes one or more particles having a specific characteristic that responds to an electric field somewhat differently than another group of one or more particles having a different characteristic. Multiple particles in the same group share the same or very similar size, charge, and/or resistance to movement. Because a tube, such as that used in traditional electrophoresis, can also function as a waveguide, optical frequency domain reflectometry (OFDR) may be used to determine the location of different chemical components along the capillary. Any tube that can function as a waveguide may be used.

OFDR is highly effective at performing high resolution distributed measurements of a scattering profile along the length of a waveguide. Scattering of light along the waveguide is related to the local index of refraction at a given location. Two consecutive measurements can be compared to detect local changes of index of refraction along the length of the waveguide by detecting changes in the scattering profile. The inventor recognized that various materials have different indices of refraction due to the respective particles that compose the material. Again, the term particle refers to a member of a group with one or more particles. A group is defined by a particular characteristic, composition, and/or structure such that for multi-member groups, each particle shares a similar characteristic, composition, and/or structure to the other particles of that group. Examples of particles include but are not limited to ions, molecules, polymers, proteins, amino acids, nucleic acids, DNA, peptides, aggregate structures such as cells, cell organelles, viruses, etc. The inventor realized that OFDR can be advantageously used to monitor the migration of a group though a waveguide by monitoring changes in local index of refraction from measurement to measurement. An OFDR system has very good resolution. For example, when swept over light wavelengths from 1520 nm to 1560 nm, an OFDR may have a spatial resolution of 20 microns, with a total range in the tens of meters.

Figure 5:
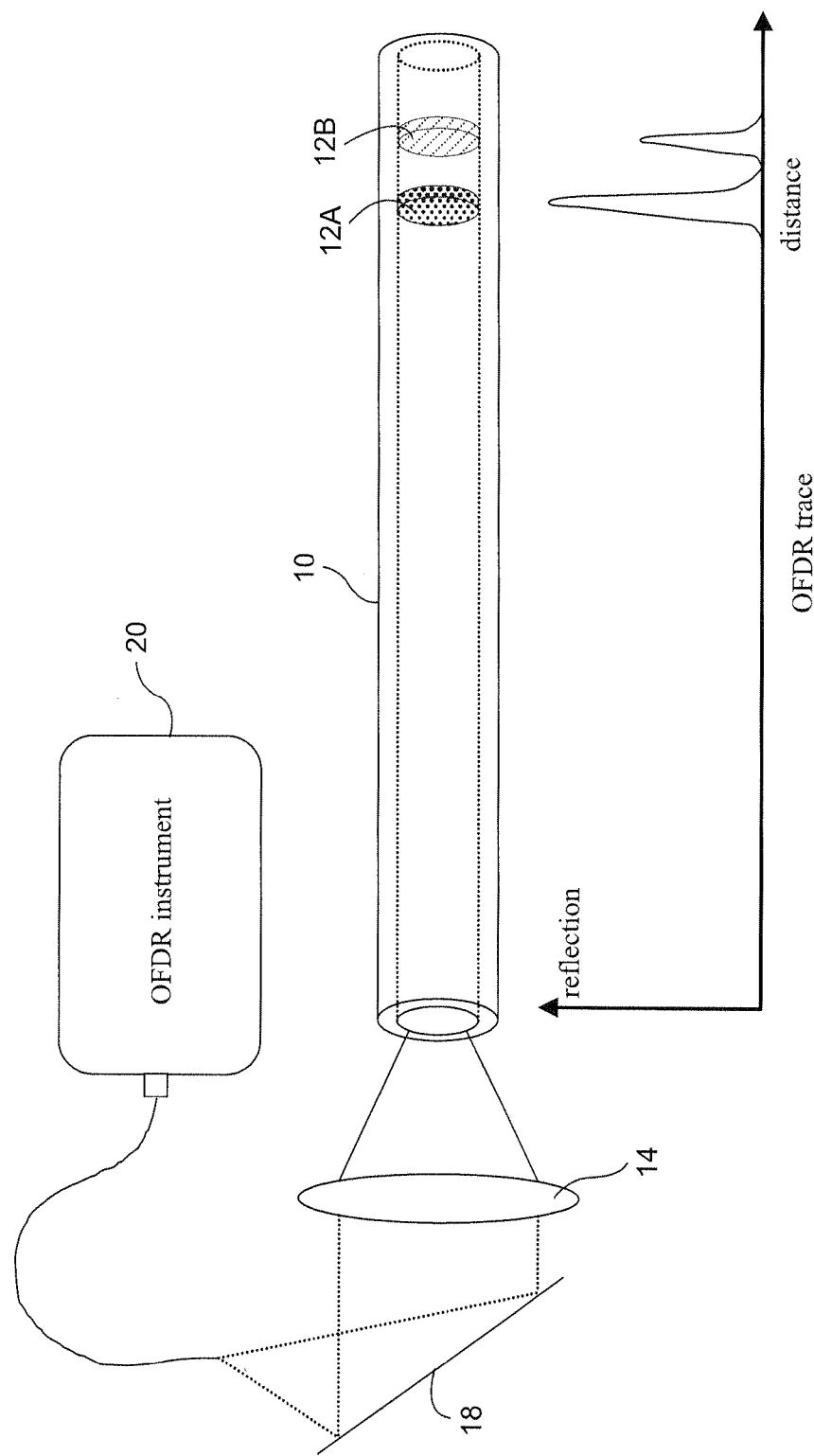
FIG. 5 is a non-limiting example of an optical frequency domain reflectometry (OFDR) instrument for detecting the distribution of particles in a tube.

FIG. 5 is a non-limiting example of an OFDR instrument 20 for detecting the distribution of particles in a tube 10 that contains a medium. Particles within a medium are subjected to a restrictive force that impedes motion of the particle through the medium. Liquid fluids are non-limiting examples. This restriction must be sufficient so that diffusion of the particles through the medium does not prevent groups of particles from forming along the length of the tube. Particles are transported through the medium within a tube by a driving force that overcomes the restrictive force imposed on the particle by the medium. Example, non-limiting driving forces are gravity and electrical potential. In the case of gravity, the setup only requires that the tube be placed in a configuration with a sufficient vertical component and the medium be configured to allow transport of the particle through the medium on a reasonable timescale.

Light from the OFDR instrument 20 is coupled into one end of the tube 10 via a mirror 18 and lens 14. Although a Fresnel waveguide may be used to direct OFDR light into the tube 10, the interior surface of the tube waveguide may be modified to provide better guiding of light with less loss, which is desirable for example in applications with longer tube lengths that allow more diverse groups of particles to be separated.

That light guided in the tube, (the tube functions as a waveguide), reflects back toward the OFDR instrument 20 if it encounters a change in the index of refraction of the solution in the tube. That reflection is detected and used by the OFDR instrument to generate a peak in a time-domain trace that is related to a distance along the tube. Hence, when light encounters a group of particles along the tube, a local change in index of refraction of the guiding medium occurs, and light is backscattered to the OFDR instrument. Over time, the generated peak in time domain trace for that group will migrate as the group of particles migrates along the length of the tube. Separate peaks are generated for separated groups of particles. Each peak may be used to determine a location of its corresponding group of particles along the tube 10. FIG. 5 shows two groups 12A and 12B with two associated OFDR detected reflections.

In order to conduct OFDR-based measurements, an OFDR instrument 20 makes an initial scatter measurement of the tube 10 to serve as a reference scatter pattern against which subsequent measurements may be compared. A solution containing multiple different particles, e.g., different chemical species, is provided at one end of the tube. However, the OFDR measurement technique described does not require that the mixed solution be placed at either particular end of the tube. With the solution present at one end of the capillary, a voltage is applied across the capillary, and different chemical species (in this example) begin to migrate along the capillary at different, characteristic velocities. After some period of time, during which the different particles, e.g., chemical species, have begun to separate along the tube due to different characteristic propagation velocities, a second OFDR measurement is made, and compared to the reference OFDR measurement.

The comparison can include either amplitude changes or phase changes, with phase changes being the more sensitive indicator. The slope of the phase change is an indication of the local index of refraction, and so regions where the slope of the phase change is above or below zero indicates particles not originally present when the reference measurement was performed. These regions of differing slope represent different groups of particles, similar to the plates or bands detected by electrophoresis. OFDR may be used to measure the location of the plates along the full length of the capillary at anytime during the separation process. As a result, although a single OFDR measurement may be performed, e.g., at the end of some process, multiple OFDR measurement scans can be made at essentially no cost in time or material.

Figure 6:
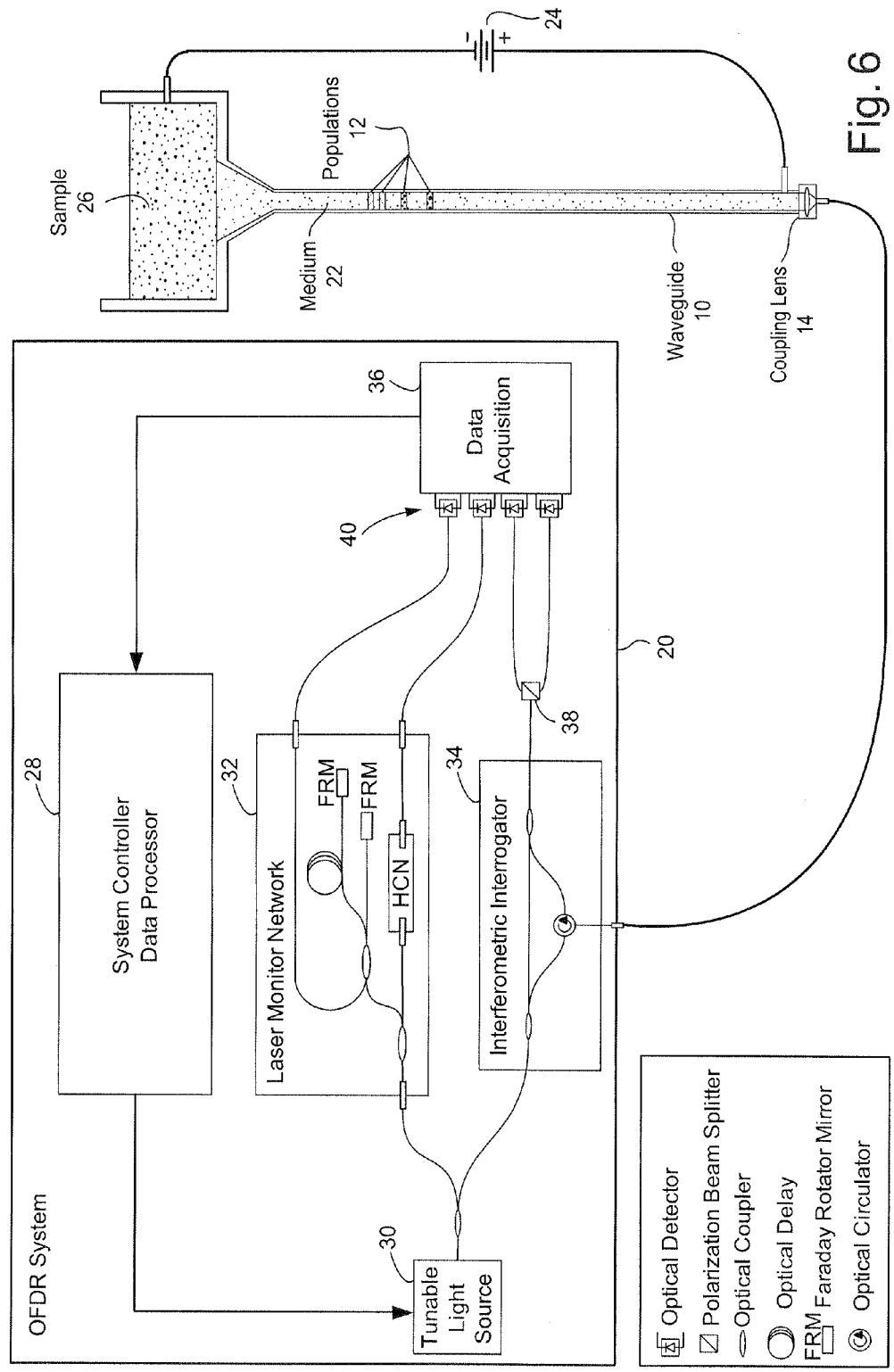
FIG. 6 is a non-limiting example setup of an OFDR system used to monitor local changes of index of refraction along the length of a media filled tube in which an electrical potential is placed across the tube to drive the motion of particles through the tube.

FIG. 6 is a non-limiting example setup of an OFDR system 20 used to monitor local changes of index of refraction along the length of a tube 10 filled with a medium 22 in which an electrical potential 24 is placed across the tube 10 to accelerate the motion of particles through the tube. Another example embodiment does not include the electrical potential but instead relies on gravity as the driving force to move sample particles supplied at the top of the tube 10 down along the tube. However, in the example embodiment shown in FIG. 6, the electrical potential 24 placed across the tube 10 further accelerates the movement of particles through the tube 10.

Different groups 12 of particles move at different speeds and therefore separate along the tube into distinct, detectable groups. A sample solution of particles is 26 fed into the tube 10 by gravity feed or some other feeding mechanism. As explained above, the driving force pulls the particles through the medium 22 within the tube. At a given time, various particles will have traveled a greater distance along the length of the tube based on each particle's respective resistance to movement through the medium and the effect of the driving force on that particle.

A tunable light source 30 is swept through a range of optical frequencies. This light is split with the use of optical couplers and routed to two separate interferometers. The first interferometer serves as an interferometric interrogator 34 and is connected to a length of sensing fiber 35. Light enters the tube 10 through the measurement arm of the interferometric interrogator 34. Scattered light along the length of the tube 10 is then interfered with light that has traveled along the reference arm of the interferometric interrogator 34. The second interferometer is within a laser monitor network 32 which measures fluctuations in the tuning rate as the light source 30 scans through a frequency range. The laser monitor network 32 also contains a Hydrogen Cyanide (HCN) gas cell which is used to provide absolute wavelength reference throughout the measurement scan. A series of optical detectors 40 convert the signals from the laser monitor network 32, gas cell HCN, and the interference pattern from the sensing fiber 35 to electrical signals for a data acquisition unit 36. A data processor 28 uses the acquired electrical signals to extract the scattering profile along the length of the tube 10 as is explained in more detail below in conjunction with FIG. 7.

Figure 7:
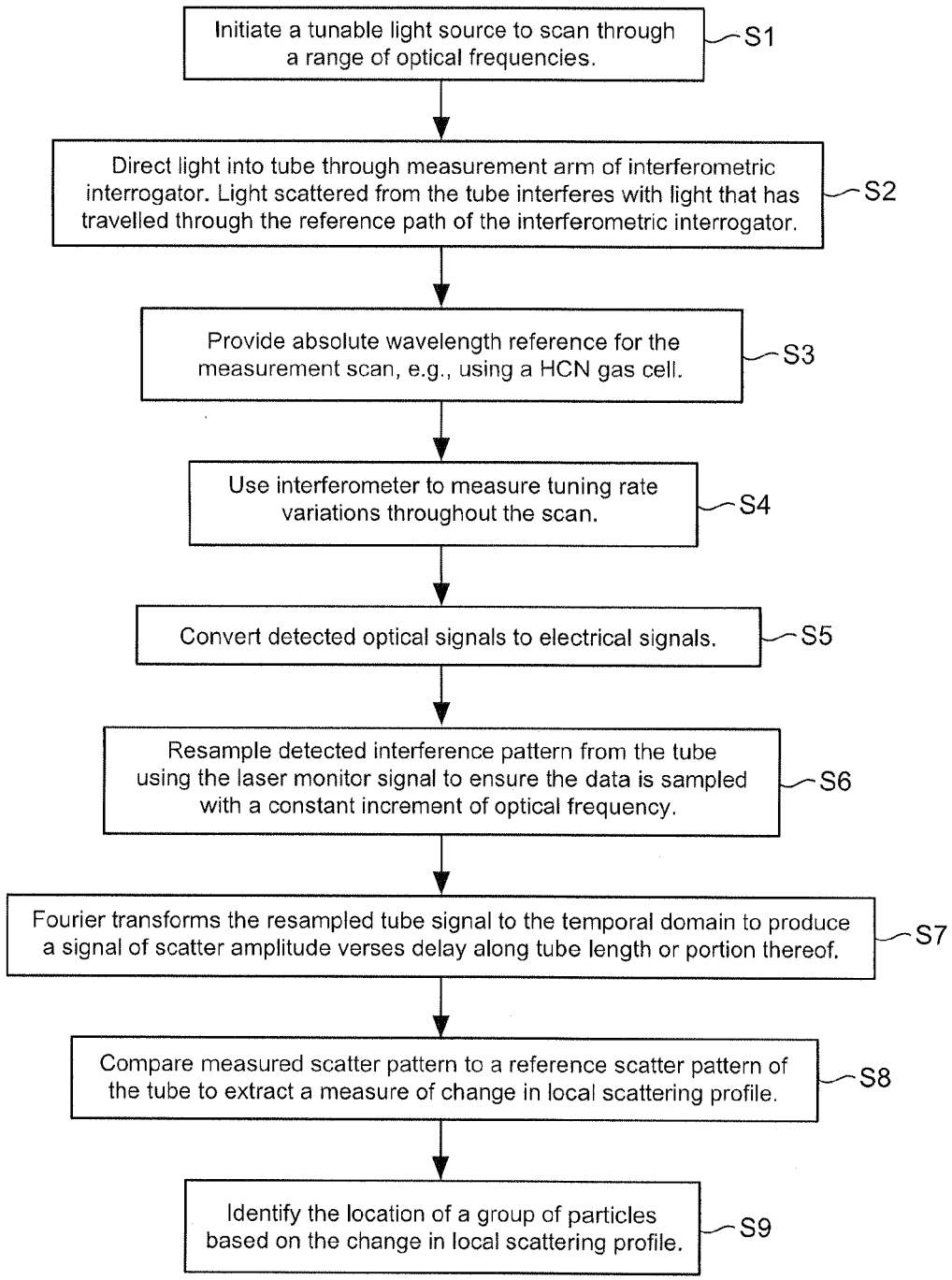
FIG. 7 is a flowchart diagram of non-limiting, example distributed measurement procedures using an OFDR system.

FIG. 7 is a flowchart diagram of non-limiting, example distributed measurement procedures using an OFDR system. In step S1, the tunable light source is swept through a range of optical frequencies and directed into the tube via the measurement arm of the interferometric interrogator (step S2). Scattered light along the length of the tube interferes with light that has traveled through the reference path of the interferometric interrogator. An absolute wavelength reference is provided for the measurement scan (step S3), and tuning rate variations are measured (step S4). Optical detectors convert detected optical signals into electrical signals (step S5) for processing by the data processor 28. The interference pattern of the sensing fiber is preferably resampled using the laser monitor signal to ensure the detected signals are sampled with a constant increment of optical frequency (step S6). Once resampled, a Fourier transform is performed to produce a tube scatter signal in the temporal domain. In the temporal domain, the scatter signal depicts the amplitude of the scattering events as a function of delay along the length of the tube (step S8). Using the distance light travels in a given increment of time, this delay is converted to a signal measure of length along the tube. In other words, this signal depicts each scattering event as a function of distance along the tube.

The sampling period is referred to as the spatial resolution and is inversely proportional to the frequency range that the tunable light source was swept through during the measurement. It can be shown that this scattering profile is highly repeatable. Hence, an OFDR measurement is performed with no particles introduced into the tube medium and stored in memory to serves as a reference scattering profile for the tube. A measurement from step S8 is compared to this reference pattern of the tube to determine a measure of change in the local scattering events along the length of the tube. Based on the change in local scattering profile, the location of each different group of particles present in the tube is determined (step S9).

The inventor realized that when comparing a measurement scan to a baseline scatter pattern, a high degree of sensitivity is achieved by considering the optical phase response along the length of the tube 10. The amount of optical phase accumulated when light travels a given physical distance is based on the optical path length. In optics, the optical path length is defined as the physical distance of a material multiplied by the refractive index of the material. In other words, light launched through a material will appear to have traveled a greater or lesser distance than the actual physical length of a material based on the index of refraction of that material. Index of refraction is related to the density of the material. Thus, as particles travel along the length of the tube 10, the apparent density of the transportation medium 22 varies at locations along the tube 10. As the density changes, the optical path length changes, and light accumulates a different amount of optical phase relative to the reference state. The change in optical phase may be determined by extracting the angle between the imaginary and real components of the product between the complex-valued OFDR scatter pattern measurement and the conjugate of the complex-valued OFDR reference scatter pattern.

If no particles have traversed along the length of the tube, then the density and the resulting index of refraction are unchanged along the length of the tube. A phase comparison between an OFDR measurement at this point and the reference OFDR measurement results in an unchanging/constant phase response. When the sample is introduced into the tube, the driving force causes the particles in the sample to traverse along the tube and separation occurs based on the average rate at which a given particle traverses through the medium 22. A group of particles form as the average speed of some particles will likely be similar, and thus, a local change in density may be observed. The local change in density causes a change in the local index of refraction, and the measurement light accumulates a different level of optical phase as the light travels a different optical path length. Thus, the location of a group of particles may be determined by detecting a phase response between the OFDR measurement and the reference scatter patterns.

Recall that a limitation of current techniques is based on the monitoring of a single point along the length of the tube to identify when a group passes that location. Groups can only be detected when they traverse the detection region at a point along the length of the tube. With an OFDR based approach, a snap shot of the entire tube length is captured and the locations of all groups are identified at a given time along the entire length of the tube. Thus, the first signs of separation can be determined without waiting for the group to pass a location along the length of the tube. This greatly reduces the time required to identify separation and also provides information regarding dynamics of the groups if several OFDR measurements are compared through time.

There are several refinements that may be made to enhance operation. Regarding coupling light into the tube 10, it is advantageous to consider the mechanical design of the tube. The smallest size of the interior diameter (ID) of the tube may be restricted by the ability of the OFDR system to analyze the very small volume of sample present and the interference of the tube wall. However, some properties of the tube may be improved with smaller tube diameter such as heat dissipation and current draw associated with the voltage source 24 in the embodiment shown in FIG. 6. Lower currents mean that higher voltage sources can be employed which increases separation rate and resolution. A smaller diameter means that heat is more readily dissipated leading to lower temperatures, and therefore lower diffusion, which leads to higher resolutions and shorter separation time. Thus, it may be advantageous to develop a tube with a small inner diameter. For example, an inner tube diameter of less than 10 μm provides an advantage of being a single mode optical system. In single mode optical operation, the light is confined to a single path of propagation down the waveguide which produces excellent OFDR readings.

Figure 8:
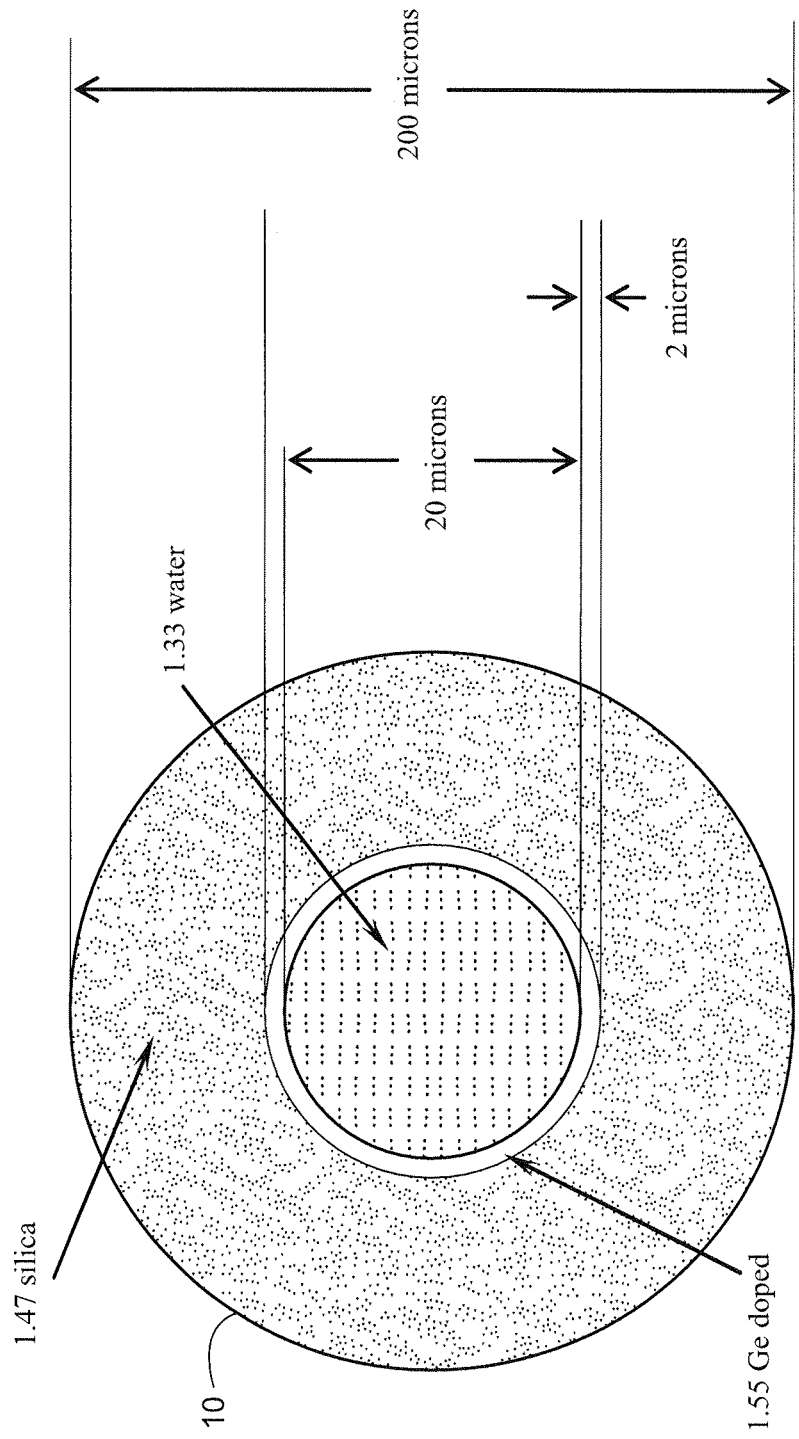
FIG. 8 is a non-limiting example increasing guiding properties of the tube by providing a narrow ring of higher index material before entering the lower index of the pure glass.

Simple Fresnel waveguides are lossy, and the light guiding effect of the tube waveguide may be improved by doping the interior of the tube with a high index material and creating a small barrier to the light escaping the center of the tube. FIG. 8 is a non-limiting example embodiment that increases wave guiding properties of the tube 10 which in this example is assumed to be glass 42. A narrow ring 43 of the glass is doped so that it has a higher index of refraction that of the glass 42 in general. This narrow ring might be Ge-doped to have an index of refraction of 1.55 which is higher than the index of refraction of glass at 1.47. In this example, the medium is water having an index of refraction of 1.33. The ring 43 thus reduces the amount of light escaping from the tube making for a better scatter measurement signal.

Figure 9:
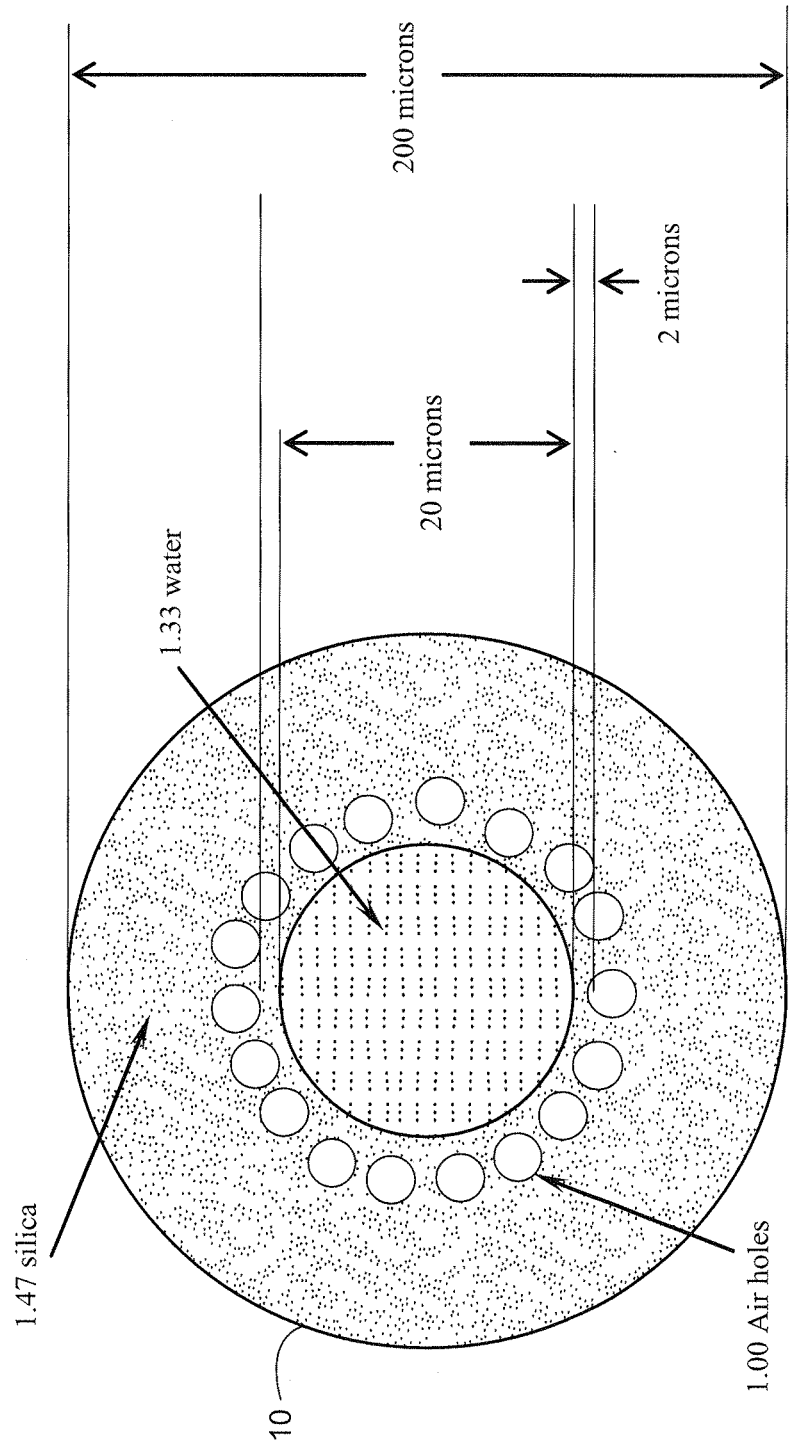
FIG. 9 shows arrays of holes in the glass which may be used to form diffraction gratings that guide light in an air or liquid core. These "holey" fibers perform well as tubes.

FIG. 9 shows another example embodiment of a tube 10 in which an array of holes 44 in the glass tube 10 is used to form diffraction gratings that guide light through the medium, which again in this example is water. These "holey" fibers are example capillaries that serve well as waveguides. The sample is transported through the inner diameter of the tube, but the array of holes surrounding this inner diameter allows very specific control of the index of refraction at this interface. A waveguide is constructed by ensuring there is a sufficient index mismatch between the inner core, or the transportation medium in this case, and the surrounding cladding glass. Thus, this solution offers a degree of flexibility in designing a tube that is ideal for a given transportation medium.

Figure 10:
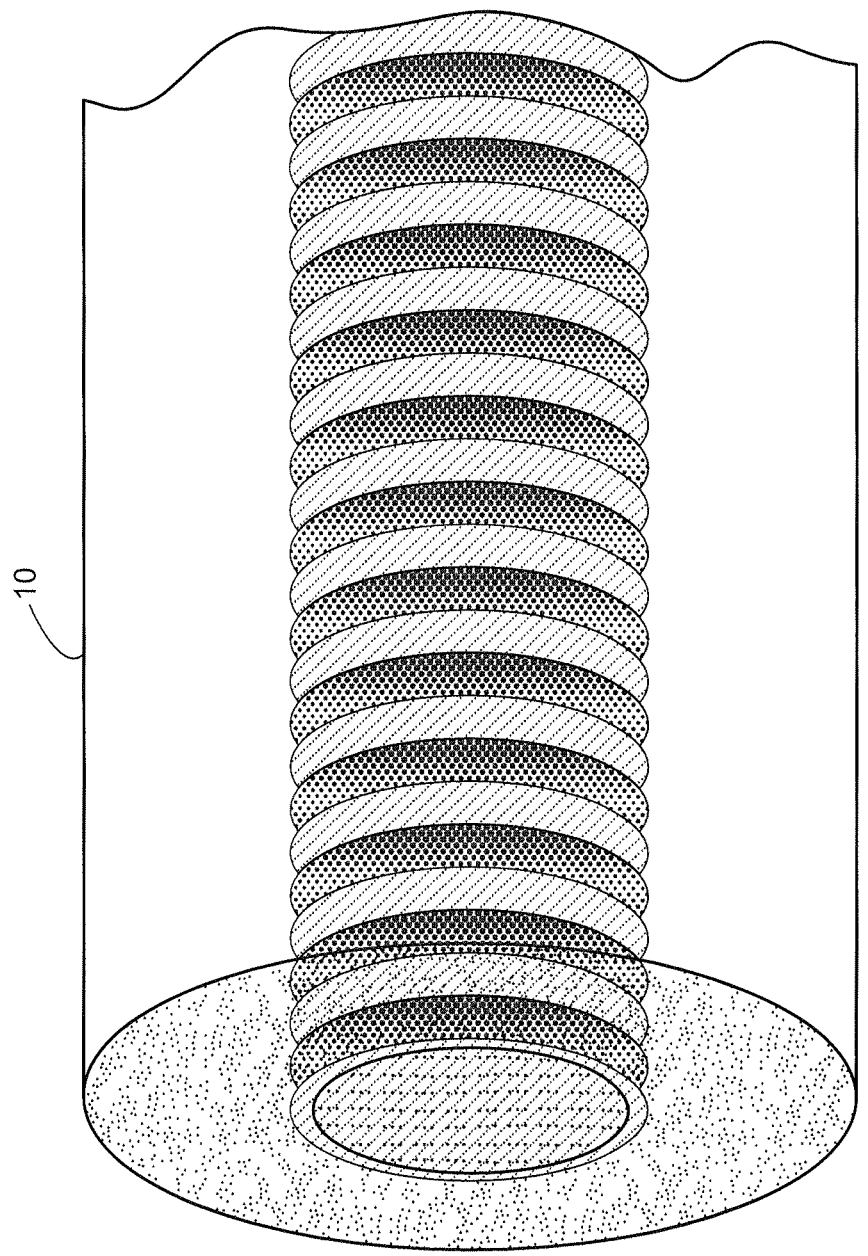
FIG. 10 illustrates a Bragg grating induced in the wall of the capillary which may be used to detect small changes in the effective index of refraction of the transportation medium within the tube.

Robustness may be further increased by taking advantage of an optical property of the light guiding tube. The local change in the index of refraction of the transportation medium caused by a group of particles traveling through the tube produces a reflection. But the change in index of refraction may be so gradual that the reflection is not easily detectable. The tube inner wall scatters substantial amounts of light, which can be readily detected. For example, a weak Bragg grating may be created in the tube inner wall and its distributed scatter may be measured. Small shifts in the resonance of the Bragg grating indicate similar shifts in the index of refraction of the group of particles at that position in the grating. Since OFDR can measure the resonance of a Bragg grating at different locations along the tube with excellent resolution, e.g., on the order of 50 microns, OFDR is an effective way of detecting the presence of dissolved molecules for example. In fact, the inventor has demonstrated OFDR sensitivities of 1 ppm over 1 cm and 10 ppm over 1 mm. FIG. 10 illustrates a Bragg grating 45 in the tube inner wall which may be used to detect small changes in the index of refraction of the water within the capillary.

Figure 11:
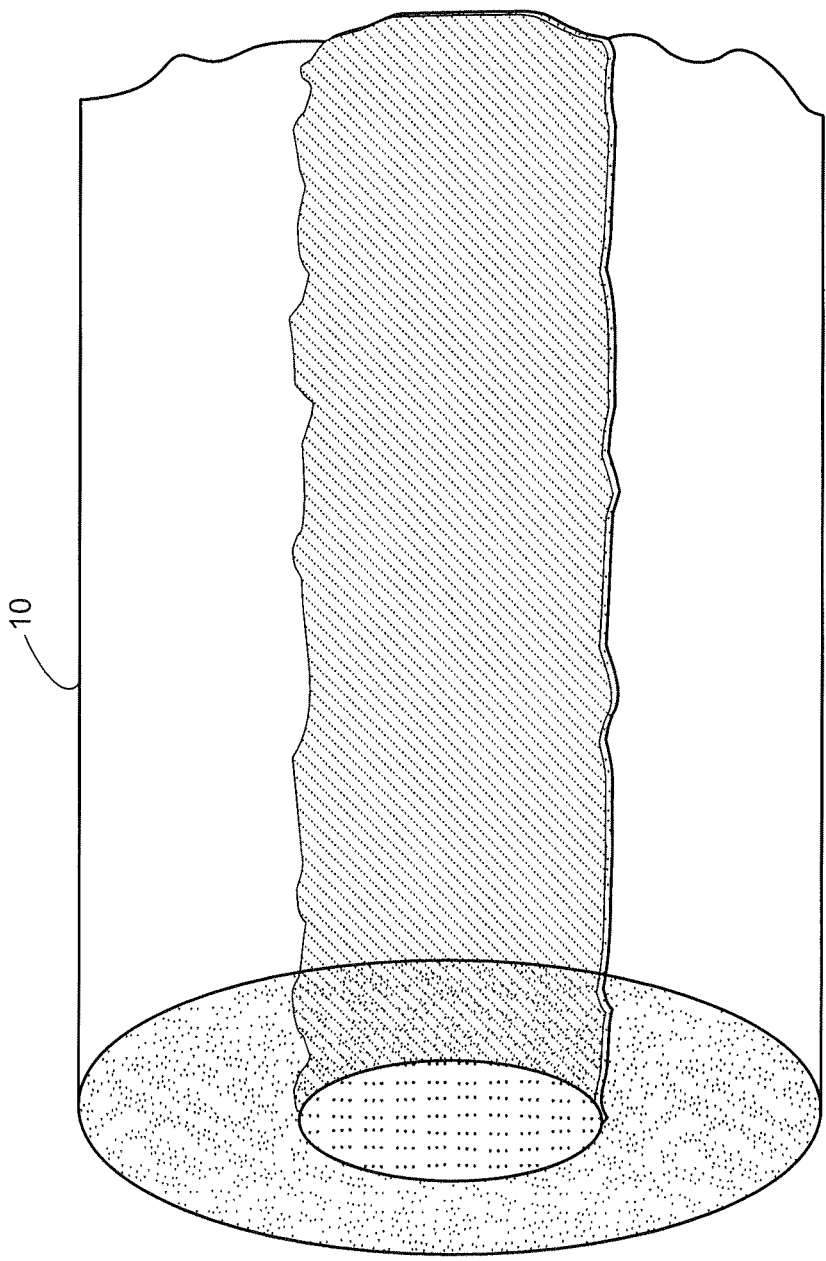
FIG. 11 illustrates how scatter from defects (roughness) of the interior tube may be used to provide information about local index of refraction.

The inventor has also demonstrated in standard optical fiber that the distributed change in local index may be detected using disordered scatter in the tube itself with sensitivities only slightly lower than that of Bragg gratings. See for example commonly-assigned U.S. Pat. No. 6,545,760, incorporated herein by reference. Therefore, the distributed changes in index can be measured with a good resolution, e.g., on the order of a few mm, using inherent scatter from the tube wall without special preparation. FIG. 11 illustrates another example embodiment in which scatter from defects (roughness) of the interior tube may be used to provide information about local index of refraction. In previous examples, it was discussed that a group of particles scatters light due to a local index of refraction change in the medium. In some cases, this change may be too subtle to scatter enough light for accurate detection. However, one can utilize light that scatters off the irregularities of the tube wall to produce a more sensitive detection scheme. In this case, as the group of particles causes a subtle variation in index of refraction, the index of refraction interface between the medium and the wall of the tube will change causing more light to be scattered from the irregularities in the wall of the tube. Thus, the location of a group of particles can be identified as it is correlated to an increase in scattering of light off the walls of the tube.

Figure 12:
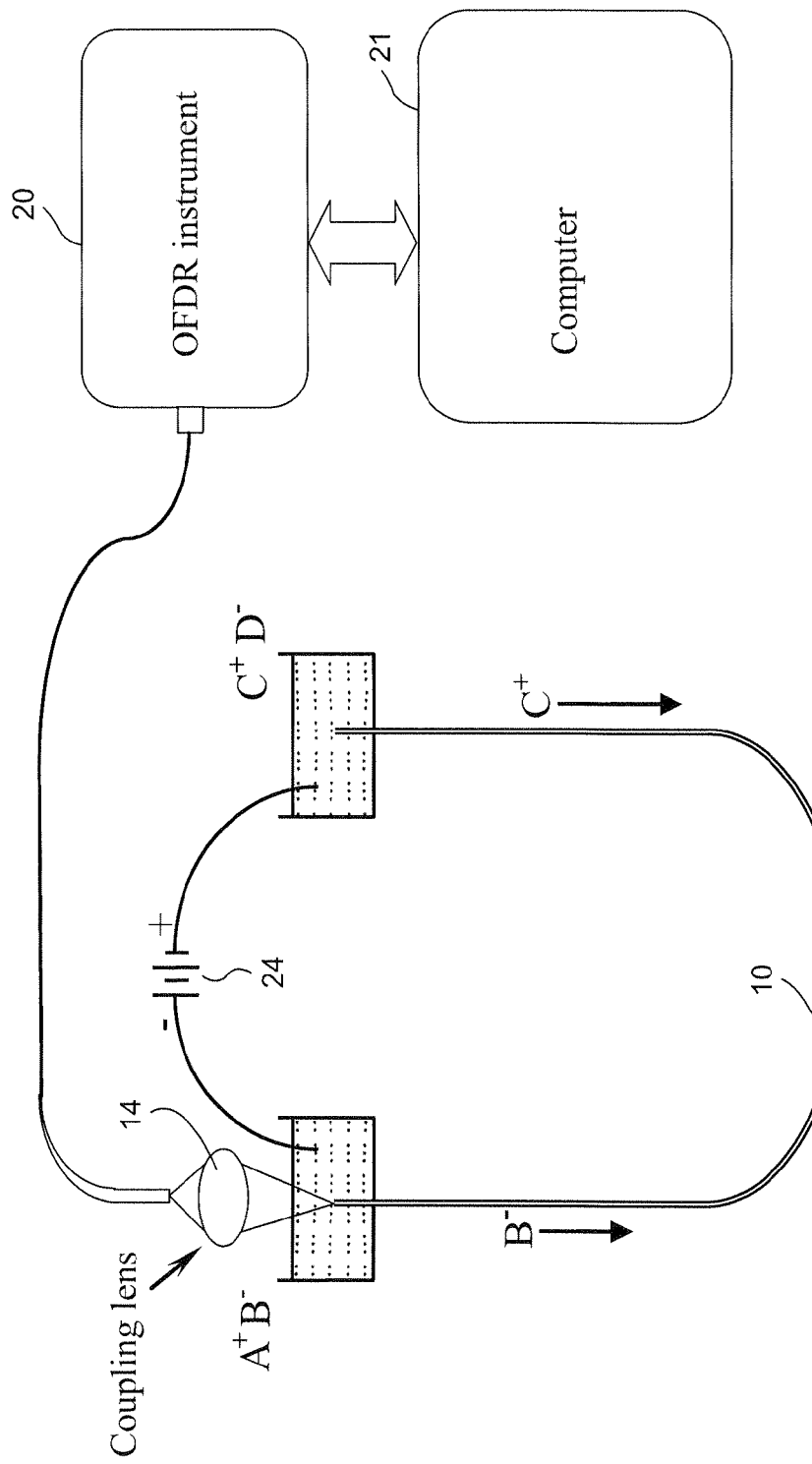
FIG. 12 is a diagram of a capillary electrophoresis system read-out using an OFDR based instrument in accordance with a non-limiting example embodiment.

FIG. 12 is a diagram of a capillary electrophoresis system read-out using an OFDR based instrument in accordance with a non-limiting example embodiment. Ions and the voltage source polarity are shown. This embodiment shows that different sources of particles may be introduced into the tube at both ends. Positive ion particles like C+ are attracted to the negative terminal of the voltage potential 24, and negative ion particles like B− are attracted to the positive terminal of the voltage potential 24.

Figure 13:
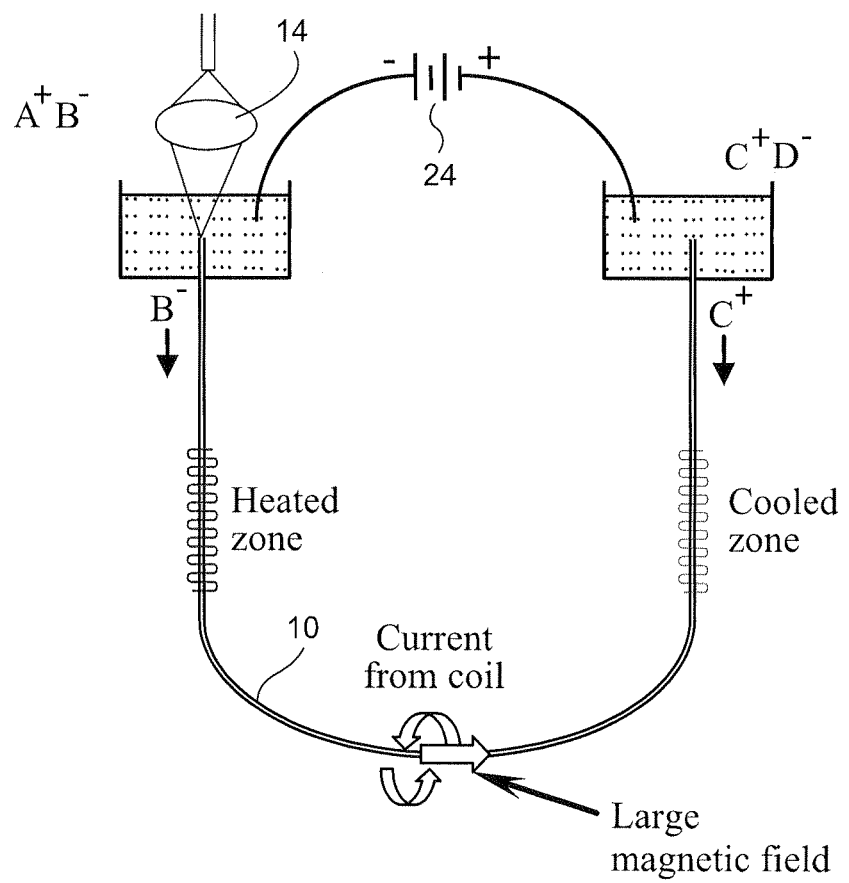
FIG. 13 shows different conditions being applied to different zones of the tube to be detected and resolved using OFDR instrument in accordance with a non-limiting example embodiment.

The example embodiment shown in FIG. 13 is similar to that shown in FIG. 12 but also shows different conditions being applied to different zones of the tube 10. Example conditions include heating and/or cooling and application of a magnetic or other field. These different conditions will allow one to modify the dynamics of the groups as they traverse these regions. As the location of all groups along the length of the tube can be monitored through time with the OFDR technique, this provides an advantage to extract information describing the dynamics of the particles which is not obtainable in conventional electrophoresis techniques.

As a non-limiting example, changing the temperature of the transportation medium in the tube can affect the binding properties of the protein linked ions moving through the medium. This affects the transport velocity of unknown molecules as they stop binding or begin binding to these known protein linked ions. An OFDR measurement readout allows observation of these changes as the molecules move through zones of different temperatures. Further, subjecting the medium to a magnetic field may also cause shifts in orbital levels that will in turn change the binding properties of the molecules. The magnetic field may also directly affect the index of refraction of the sample, which can provide additional information about unknown particles. A magnetic field may cause the particles in a group to align with respect to the field. It is feasible that more light will be back scattered due to the overall shape and orientation of the particles within a group. Charting index of refraction (permittivity in this case) as a function of magnetic field or temperature is another useful function that this instrument can provide as it gives further insight to the structure and physical properties of particles.

Extracting this additional information from the particles is not obtainable in conventional electrophoresis techniques. Detection based on a single monitoring location forces one to only analyze the aggregate effect that the group of particles experiences. By applying such conditions along the tube and having a system that can detect the position of particles along the length of the tube, their individual and local effects may be directly observed.

Figure 14:
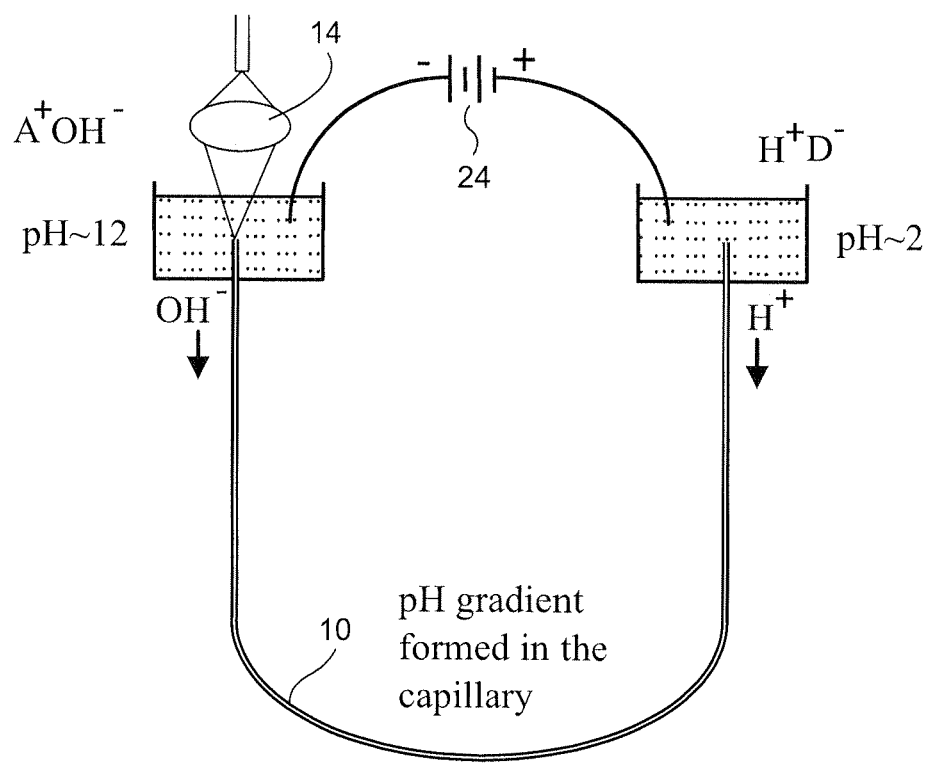
FIG. 14 illustrates a non-limiting example embodiment for producing a pH gradient in the tube and reading out the time-dependent spatial distribution of unknown molecules.

FIG. 14 illustrates a non-limiting example embodiment for producing a pH gradient in the capillary tube and reading out the time-dependent spatial distribution of unknown molecules. The pH of the solution in the tube effects the ionization of proteins. As a result, and wide range (e.g., from 1 to 13) of pH's may be used for the tube medium. The rate at which a group of particles travels along the length of the tube is proportional to the net charge of the particles. Hence, by changing the pH, the overall net charge on a particle will be changed, and the rate at which that particle traverses the through the transportation medium will vary. By observing several rates of motion of particles in various pH solutions, information regarding the physical structure or composition of the particles within a group may be determined.

Typically, traditional capillary electrophoresis cannot multiplex the detector because the detector must observe a single position near the end of the capillary continuously. Due to the complexity and cost of this setup, it is not practical to setup a large number of detection points along the length of the capillary. Further, due to the size of these setups, it is not possible to continuously monitor every location along the length of the capillary to a spatial resolution comparable to an OFDR-based detection scheme. As a result, the technology does not multiplex well. By having a system that can interrogate a tube by measuring the position of all groups of particles in the medium at a large number of locations along the tube, a system like that shown in FIG. 6 can interrogate multiple tubes in a single test.

Figure 15:
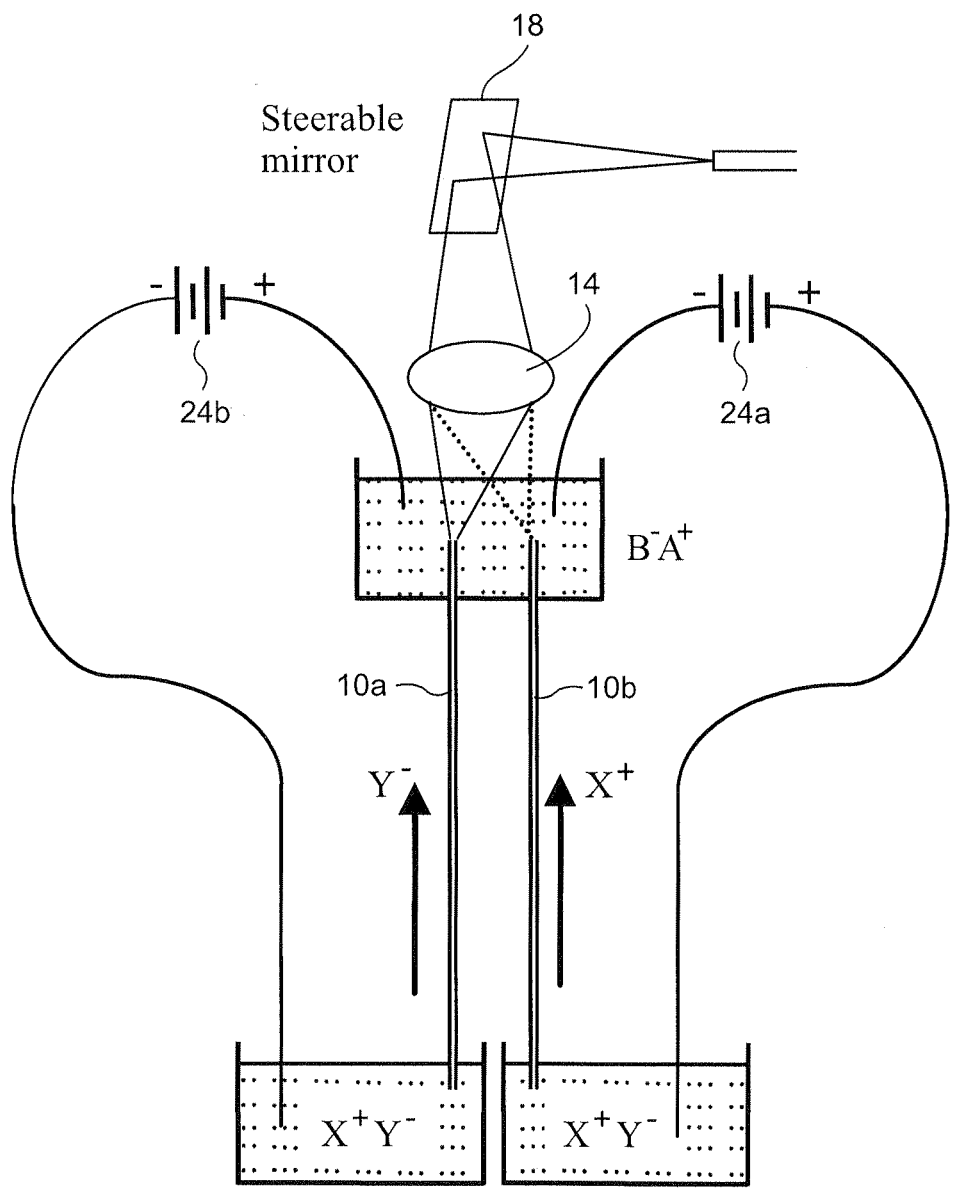
FIG. 15 illustrates a non-limiting example embodiment of a multiplexed use of the OFDR read-out in addition to measuring anions and cations simultaneously with two tubes and a single OFDR system.

FIG. 15 illustrates a non-limiting example embodiment of a multiplexed use of the OFDR read-out in addition to measuring anions and cations simultaneously with two tubes and a single OFDR system. Using OFDR combined with a steerable mirror 18 to redirect the OFDR probe beam, the OFDR system can be steered to simultaneously measure the positive and negatively charged ions in a solution in multiple tubes 10a and 10b.

Figure 16B:
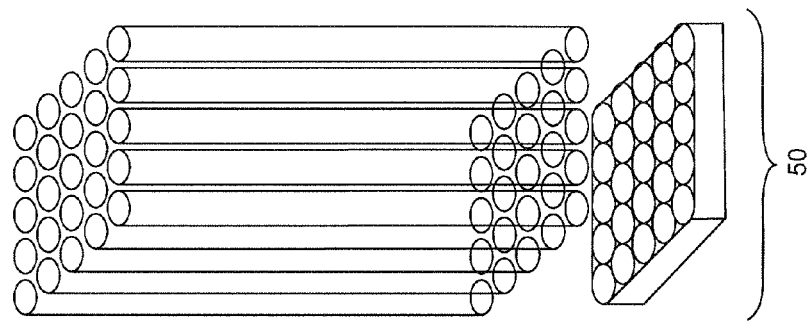
FIG. 16 illustrates a non-limiting example embodiment of a dense multiplexing scheme for capillary electrophoresis using an OFDR system and a steerable mirror.
Figure 16A:
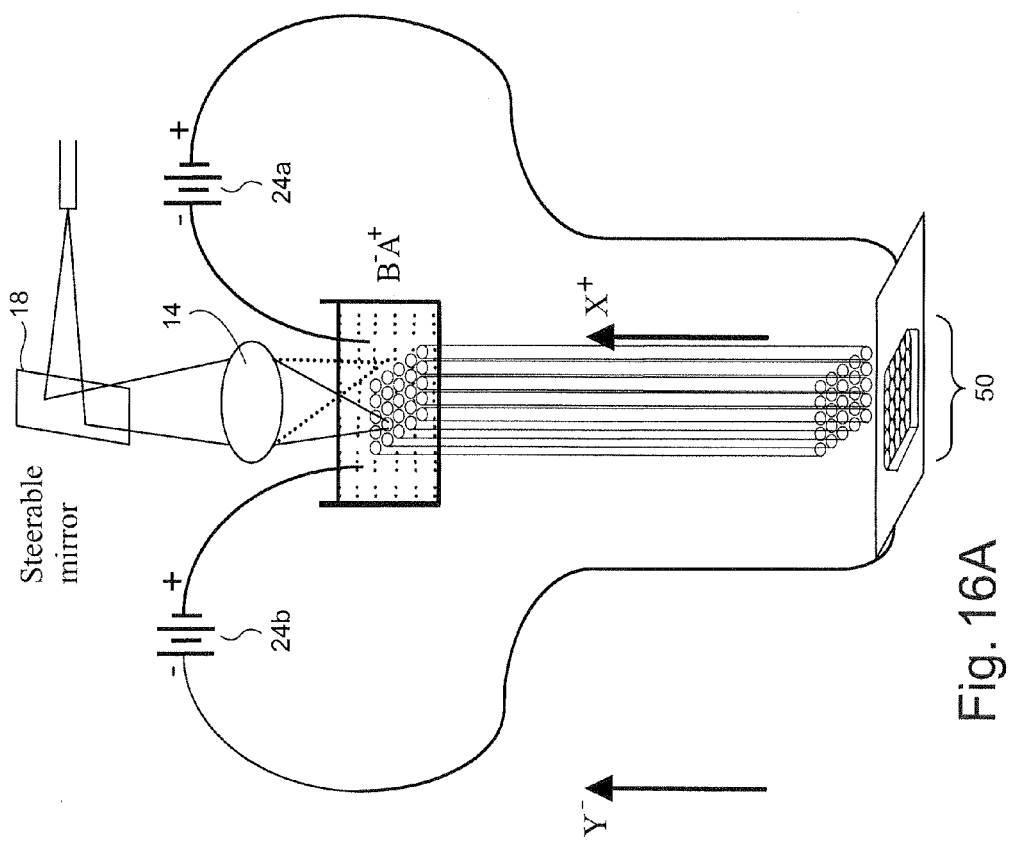

FIG. 16 illustrates a non-limiting example embodiment of a dense multiplexing scheme for capillary electrophoresis using an OFDR system and a steerable mirror. Using a mirror 18 to steer the OFDR probe light into different tubes allows, for example, many tubes (e.g., a 20×20 tube array where each tube is on a 500 micron spacing) to be interrogated with a single OFDR. In this non-limiting example, the short distances make possible a large number, e.g., 500, scans per second or more. This massive parallel analysis is useful, for example, in drug discovery applications Drug discovery applications often require substantial statistical analysis which implies that many iterations of the same experiment must be conducted. Thus, the ability to multiplex a massive group of similar samples will greatly expedite the analysis of a given drug.

The technology is flexible and may adapt to a particular application. For example, various gels will have a varying pore size, and an optimal pore size can be chosen based on the size of a given particle to be separated. Further, different methods of varying the driving force can be implemented to adapt to the size of the particles. The technology described above may also be used to separate macro and microscopic particles.

Although various embodiments have been shown and described in detail, the claims are not limited to any particular embodiment or example. None of the above description should be read as implying that any particular member, step, range, or function is essential such that it must be included in the claims scope. The scope of patented subject matter is defined only by the claims. The extent of legal protection is defined by the words recited in the allowed claims and their equivalents. All structural and functional equivalents to the members of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC §112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. An optical interrogation system for measuring local changes of index of refraction of a medium contained within a light guiding tube, comprising:
   an optical interferometric interrogator;
   optical detection circuitry; and
   a data processor configured to:
   initiate a sweep of the light source and guide light from an interrogating light source into a medium contained by a tube which restricts movement of particles provided into the tube, where the medium is subjected to a driving force that overcomes resistance to movement of particles through the medium in the tube, detect via the optical interferometric interrogator an optical interference pattern associated with a group of particles having moved in the tube as a result of the driving force, and based on the detected optical interference pattern, identify a current location of the group of particles in the tube.

2. The optical interrogation system in claim 1, wherein the optical interrogation system is an optical frequency domain reflectometry (OFDR)-based system, the interrogating light source is a tunable laser, and the detected optical interference pattern indicates back scatter amplitude as a function of time along the tube.

3. The optical interrogation system in claim 2, wherein the driving force causes a first group of particles in the medium to move through the tube at a different speed than a second different group of particles in the medium, and wherein the data processor is configured to detect a first location of the first group of particles in the tube medium and a second location of the second group of particles in the tube medium based on different optical interference patterns detected for the first and second groups.

4. The optical interrogation system in claim 3, wherein each of the first and second groups of particles causes a local change in index of refraction of the medium and the local change in index of refraction changes the optical interference pattern as compared to a reference optical interference pattern, and wherein the data processor is configured to identify the location of each of the first and second group of particles in the tube based on the changed optical interference pattern.

5. The optical interrogation system in claim 1, wherein the optical interference pattern is a scattering profile.

6. The optical interrogation system in claim 1, wherein the optical interrogation system is an optical frequency domain reflectometry (OFDR)-based system, the interrogating light source is a tunable laser, and the detected optical interference pattern indicates a change in optical phase as a function of time along the tube.

7. The optical interrogation system in claim 6, wherein the data processor is configured to detect multiple optical interference patterns corresponding to multiple different locations along the tube.

8. The optical interrogation system in claim 1, further comprising the tube being optically coupled to the optical interrogation system, wherein the tube is made of a first material having a first index of refraction and an inner ring of a second material having a second, higher index of refraction.

9. The optical interrogation system in claim 1, further comprising the tube being optically coupled to the optical interrogation system, wherein the tube includes an array of holes parallel to and adjacent an inner ring of the tube.

10. The optical interrogation system in claim 1, further comprising the tube being optically coupled to the optical interrogation system, wherein the inside of the tube includes one or more Bragg gratings.

11. The optical interrogation system in claim 1, further comprising the tube being optically coupled to the optical interrogation system, wherein the inside surface of the tube includes defects and wherein the data processor is configured to process back scatter from the defects to identify local changes in index of refraction.

12. The optical interrogation system in claim 1, further comprising multiple tubes being optically coupled to the optical interrogation system, wherein the data processor is configured to:

initiate a sweep of the light source and guide light from the interrogating light source into the medium contained by each tube, detect via the optical interferometric interrogator an optical interference pattern associated with a group of particles having moved in each tube, and based on the detected optical interference patterns, identify a current location of the group of particles in each of the multiple tubes.

13. The optical interrogation system in claim 12, wherein the multiple tubes are an array of tubes.

14. The optical interrogation system in claim 1, wherein an environment surrounding the tube is modified to change a response of one or more particle groups in the tube, and wherein the data processor is configured to identify a characteristic of the one or more particles in one of the particle groups based on an optical interference pattern detected from the tube subjected to the modified environment.

15. The optical interrogation system in claim 14, wherein modifying the environment includes one or more of modifying temperature, pH, and/or magnetic field.

16. The optical interrogation system in claim 1, wherein one or more properties of the transportation medium with the tube is modified, and wherein the data processor is configured to identify a characteristic of the one or more particles in one of the particle groups based on an optical interference pattern detected from the tube after the transportation medium is modified.

17. A method for measuring local changes of index of refraction of a medium contained within a light guiding tube using an optical interrogation system, comprising:

providing particles into a tube containing a medium that restricts movement of the particles;

subjecting the medium in the tube to a driving force that overcomes resistance to movement of particles through the medium in the tube, guiding light from an interrogating light source into the tube, detecting, via an optical interferometric interrogator, an optical interference pattern associated with a group of particles having moved in the tube as a result of the driving force, and based on the detected optical interference pattern, identifying a current location of the group of particles in the tube.

18. The method in claim 17, wherein the optical interrogation system is an optical frequency domain reflectometry (OFDR)-based system, the interrogating light source is a tunable laser, and the OFDR-based system detects optical interference pattern and generates information indicating back scatter amplitude as a function of time along the tube.

19. The method in claim 18, wherein the detected optical interference pattern indicates a change in optical phase as a function of time along the tube.

20. The method in claim 18, further comprising detecting multiple optical interference patterns corresponding to multiple different locations along the tube.

21. The method in claim 17, wherein the driving force causes a first group of particles in the medium to move through the tube at a different speed than a second different group of particles in the medium, the method further comprising:

detecting a first location of the first group of particles in the tube medium and a second location of the second group of particles in the tube medium based on different optical interference patterns detected for the first and second groups.

22. The method in claim 21, wherein each of the first and second groups of particles causes a local change in index of refraction of the medium and the local change in index of refraction changes the optical interference pattern as compared to a reference optical interference pattern, the method further comprising:
identifying the location of each of the first and second group of particles in the tube based on the changed optical interference pattern.

23. The method in claim 17, wherein the optical interference pattern is a scattering profile.

24. The method in claim 17, wherein the tube is made of a first material having a first index of refraction and an inner ring of a second material having a second, higher index of refraction.

25. The method in claim 17, wherein the tube includes an array of holes parallel to and adjacent an inner ring of the tube.

26. The method in claim 17, wherein the inside of the tube includes one or more Bragg gratings.

27. The method in claim 17, wherein the inside surface of the tube includes defects, the method further comprising processing back scatter from the defects to identify local changes in index of refraction.

28. The method in claim 17, further comprising:
optically coupling multiple tubes to the optical interrogation system,
initiating a sweep of the light source and guide light from the interrogating light source into the medium contained by each tube,
detecting via the optical interferometric interrogator an optical interference pattern associated with a group of particles having moved in each tube, and
based on the detected optical interference patterns, identifying a current location of the group of particles in each of the multiple tubes.

29. The method in claim 28, wherein the multiple tubes are an array of tubes.

30. The method in claim 17, further comprising:
modifying an environment surrounding the tube to change a response of one or more particle groups in the tube, and
identifying a characteristic of the one or more particles in one of the particle groups based on an optical interference pattern detected from the tube subjected to the modified environment.

31. The method in claim 30, wherein modifying the environment includes one or more of modifying temperature, pH, and/or magnetic field.

32. The method in claim 17, further comprising:
modifying one or more properties of the transportation medium with the tube,
identifying a characteristic of the one or more particles in one of the particle groups based on an optical interference pattern detected from the tube after the transportation medium is modified.

* * * * *